United States Patent
Pfeiffer et al.

(10) Patent No.: US 7,010,150 B1
(45) Date of Patent: Mar. 7, 2006

(54) METHOD FOR DETECTING AND REPRESENTING ONE OR MORE OBJECTS, FOR EXAMPLE TEETH

(75) Inventors: Joachim Pfeiffer, Bensheim (DE); Volker Wedler, Heddesheim (DE); Ulrich Orth, Laufertal (DE); Reinhard Pieper, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 09/979,892

(22) PCT Filed: May 25, 2000

(86) PCT No.: PCT/DE00/01668

§ 371 (c)(1),
(2), (4) Date: Jan. 24, 2002

(87) PCT Pub. No.: WO00/74374

PCT Pub. Date: Dec. 7, 2000

(30) Foreign Application Priority Data

May 27, 1999 (DE) ................................ 199 24 291

(51) Int. Cl.
*G06K 9/00* (2006.01)

(52) U.S. Cl. ...................... 382/128; 382/154; 382/296; 382/294; 433/29

(58) Field of Classification Search .............. 382/128, 382/120, 154, 164, 178, 279, 284, 285, 294, 382/302, 165, 276, 289, 295, 296; 433/29, 433/223; 250/559.06; 600/447, 415; 345/419, 345/629; 356/39; 377/10
See application file for complete search history.

(56) References Cited

U.S. PATENT DOCUMENTS

| | | | | |
|---|---|---|---|---|
| 4,575,805 A | * | 3/1986 | Moermann et al. | 700/163 |
| 4,837,732 A | * | 6/1989 | Brandestini et al. | 433/29 |
| 5,278,756 A | * | 1/1994 | Lemchen et al. | 600/587 |
| 5,604,817 A | * | 2/1997 | Massen et al. | 382/120 |
| 5,740,802 A | * | 4/1998 | Nafis et al. | 600/407 |
| 5,818,454 A | * | 10/1998 | Arai et al. | 345/593 |
| 6,068,482 A | * | 5/2000 | Snow | 433/223 |
| 6,093,019 A | * | 7/2000 | Morandi et al. | 433/29 |
| 6,245,017 B1 | * | 6/2001 | Hashimoto et al. | 600/447 |
| 6,480,192 B1 | * | 11/2002 | Sakamoto et al. | 345/419 |
| 6,486,888 B1 | * | 11/2002 | Fushiki et al. | 345/592 |
| 6,694,212 B1 | * | 2/2004 | Kennedy | 700/163 |
| 6,747,665 B1 | * | 6/2004 | Stoval et al. | 345/629 |
| 6,845,157 B1 | * | 1/2005 | Bingel et al. | 379/399.01 |
| 6,882,744 B1 | * | 4/2005 | Oosawa | 382/132 |
| 2002/0048393 A1 | * | 4/2002 | Oosawa | 382/132 |
| 2002/0093516 A1 | * | 7/2002 | Brunner et al. | 345/629 |
| 2003/0012423 A1 | * | 1/2003 | Boland et al. | 382/154 |
| 2004/0218792 A1 | * | 11/2004 | Spoonhower et al. | 382/128 |
| 2004/0265770 A1 | * | 12/2004 | Chapoulaud et al. | 433/24 |

\* cited by examiner

*Primary Examiner*—Barry Choobin
(74) *Attorney, Agent, or Firm*—Dykema Gossett PLLC

(57) ABSTRACT

A method for detecting and representing one or more objects, such as teeth, their preparations and their immediate environment, using a camera. A first recording is made wherein a still image is produced. The still image is blended into a current, mobile search image in at least one sub-area in the second step, so that both images are recognizable. In the third step, the camera is positioned in such a way that the search image overlaps the blended-in still image in at least one sub-area. The second recording process is initiated in a fourth step.

12 Claims, 3 Drawing Sheets

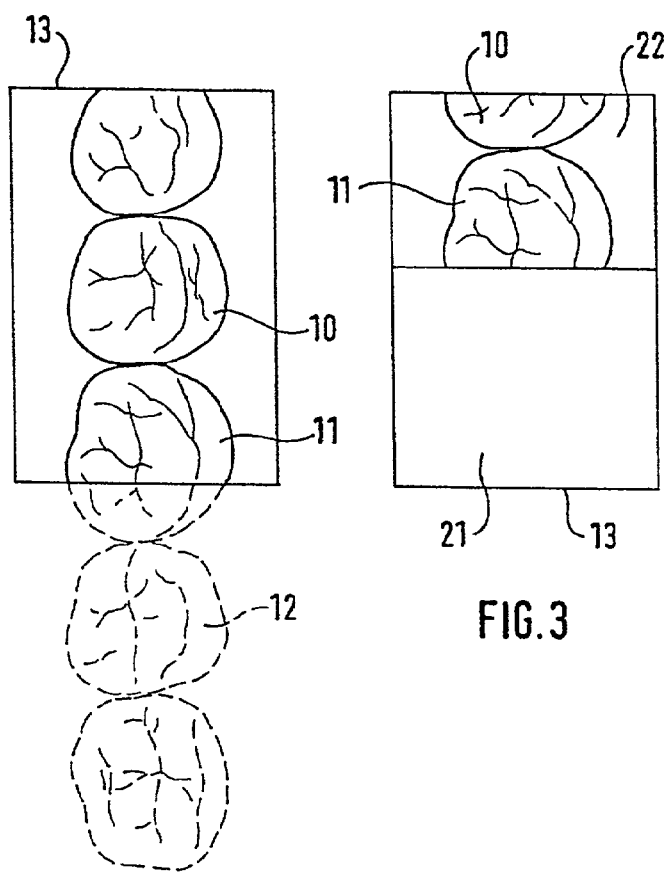
FIG. 2
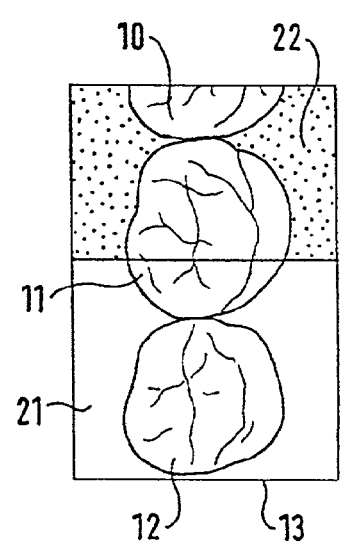
FIG. 3
FIG. 4

METHOD FOR DETECTING AND REPRESENTING ONE OR MORE OBJECTS, FOR EXAMPLE TEETH

BACKGROUND OF THE INVENTION

The invention relates to a method for detecting and representing one or more objects, for example teeth or their preparations and their immediate vicinity, using a camera for obtaining three-dimensional data. These data can be used for producing a fitting.

DESCRIPTION OF THE RELATED ART

EP 0 250 993 B1 discloses a method for spatially recording and representing teeth, their preparations and their immediate vicinity using a camera for obtaining three-dimensional data. The data is used for producing a fitting. In order to determine the suitable recording position of the camera, a reference pattern is projected to obtain data depth. First, however, a moving video search image is generated and displayed on a monitor on which the projected reference pattern does not appear. If the camera is in the desired recording position, then in response to an initiation command, an image recording sequence will proceed for generating and storing a data record. The data record contains image information items corresponding to the last search image which can be displayed in the form of a contrast image as drawing original on the monitor. The data record also contains depth values congruent with the image information, so that a construction performed on the drawing original together with the depth values defines the fitting three-dimensionally. For the construction of the fitting, the dentist inputs boundary lines using a drawing aid. An appropriate drawing aid in this case is a mouse.

In the process of producing fittings for tooth reconstruction, the spatial recording is embedded in a superordinate method which allows for different recordings to be related to one another. Such different recordings have been generated from various positions of the 3D camera with respect, i.e., for the transformation parameters which transform all the recordings into a common reference system (translation, rotation) to be determined. This correlation or, alternatively, registration of the recordings with respect to one another is achieved, in principle, by employing software methods which rotate and translate an image data record until, in the areas in which it represents the same object as another image data record with which it is intended to be correlated, it corresponds optimally to said other image data record. However, software methods of this type function only when the relative position of the images is adequately known as a result of previous measures, i.e., the images must be coarsely correlated with one another. The production of such coarse correlation is achieved in the prior art by clearly defined contours of the object (e.g. periphery) being marked in a first image through the use of a drawing aid (mouse).

When the second 3D measurement recording is created, these markings are inserted into the video search image and the measuring camera is moved into a position such that the markings correspond as well as possible to the corresponding structures on the video search image. A second measurement is then carried out in this position.

The interactive definition of the contour lines makes it necessary for the operator to continually alternate between the camera and the drawing aid during the sequence of a plurality of recordings. This is disadvantageous, particularly when different recordings of the same tooth and of its surroundings have to be correlated with one another, or when rows of teeth have to be recorded over a plurality of recordings.

BRIEF DESCRIPTION OF THE INVENTION

It is an object of the invention to provide a method for detecting and representing one or more objects in which different individual images of the same object or of adjacent objects are related to one another without using mechanical apparatuses, such as drawing aids, in the process.

According to the invention, after the production of the first recording, in a second step, the still image is inserted into a current, moving search image, at least in a sub-area, so that both images are recognizable. In a third step, the camera is positioned in such a way that the search image attains congruence with the inserted still image at least in a sub-area. And in a fourth step, the second recording is initiated.

In the interaction of the hand orienting the camera and the software processing the images, the present method enables the manual coarse correlation of two or more image data records that represent the same object in sub-areas.

The recording advantageously yields a 3D data record, that is the image data record also comprises depth values. The coarsely correlated 3D data records can then be correlated precisely by means of automatic computation methods as in the prior art. That is, the transformation parameters between the reference systems of the two individual recordings are automatically determined computationally.

In this case, the requirements made of the coarse correlation depend on the configuration of the computational correlation method and the available computing power and time. Generally it holds true that the better the coarse correlation, the faster and the more accurately the computational methods function for exact correlation. In the context of the superordinate method for producing dentures, the need arises to correlate a plurality of recordings with one another, to be precise in three variants.

In order to measure an object from different directions or distances, and to be able to detect undercuts and/or to extend the depth measurement range and/or to increase the accuracy by averaging, the first recording is carried out by applying the method according to the invention. What is achieved is that during the second and, if appropriate, further recording, only the viewing angle and the distance from the object are varied but the object always appears in approximately the same position on the image. This produces an advantageous starting position for the automatic, exactly calculated correlation.

In order to measure an object in the original state and after it has been altered in sub-areas, such as a row of teeth before and/or after the preparation of an individual tooth, the first measurement of the object in the original state is carried out and. By applying the method according to the invention, the second recording (of the changed object) is effected from as far as possible the same position of the camera as the first recording and a coarse correlation is thus achieved. The subsequent automatic exact correlation is effected using the object areas which were not altered. This procedure can also be used for progressive documentation.

By virtue of the fact that the object to be recorded in the second image has been altered relative to the object recorded in the first image, the surroundings of the altered object having remained essentially unchanged. This process makes it possible to document restorations and to detect changes to the restorations.

If the intention is to measure objects which are more extensive than the measurement zone of the camera, part of the object can be measured in a first position of the camera. Afterward, a second measurement recording is created, which covers part of the area of the first measurement recording but also captures a new part of the object. In this case, the still image is displaced by a predetermined distance and/or a predetermined angle and is thus superposed on the moving search image only in a sub-area. Using the area of overlap, the two measurement recordings are coarsely correlated by the method according to the invention, and exactly correlated according to automatic methods known per se. As a result, it is possible for successively recorded sub-images of a complete jaw to be strung together exactly and thus for a dental arch as a whole to be detected and measured.

By virtue of the fact that the first image and the second image are displaced relative to one another, the displacement amounting to at least ⅒ and advantageously ¼ of the extent of the image in the direction of the displacement, it is possible to detect one or more objects which exceed the size of the actual image zone. The correlation is effected by ascertaining identical areas and transforming the three-dimensional data obtained into a single measurement model.

The displacement and/or rotation are advantageously effected in a manner dependent on the area to be recorded using knowledge about the image information to be expected from the object to be recorded for the second image. This knowledge may be information determined from statistical evaluations or from individual peculiarities typical of the object. This means that manual displacement is unnecessary, as a result of which the operability is improved.

The above-described insertion of the first image can be done by the first image being superposed semi-transparently on the video search image during the second recording. Semi-transparently means that both image information items are superposed in such a way that they both appear superposed on the screen and can be recognized by the eye.

The representation of the image information items of the first image and of the moving video search image can also be produced by additive mixing.

It is likewise possible for the first image and the moving video search image to be represented in such a way that the image information items alternate row by row or column by column. The image information items may also be interwoven like a chessboard, i.e., the first image is represented on the "white zones" and the moving video search image is represented on the "black zones".

The combination of the image information items takes place only in the areas where both images yield information items. The image is exclusively represented at the locations where only one image yields information. As a result of this, only the areas that are crucial for assessing the positioning are represented, without disturbing superpositions taking place.

A further improvement of the manual alignment of the video search image with the first image is produced by the first image being represented in one hue, in particular in red, whereas the search image is represented in black and white or in another color.

It may be advantageous if the first image is not superposed directly, but rather as modifications thereof. Such modifications generated by image-processing means allow for the recognition accuracy to be improved.

Other objects, advantages and novel features of the invention will become more apparent from the following detailed description of the invention when taken in conjunction with the accompanying drawings.

BRIEF DESCRIPTION OF THE DRAWINGS

The method according to the invention is explained with reference to the drawing, in which:

FIG. 2 is a top plan view of the already created first recording of an object;

FIG. 3 is a top plan view of the longitudinally displaced first recording prior to the insertion of the video search image;

FIG. 4 is a top plan view of the video search image with the overlapped first recording;

DETAILED DESCRIPTION OF THE INVENTION

Figure 1:
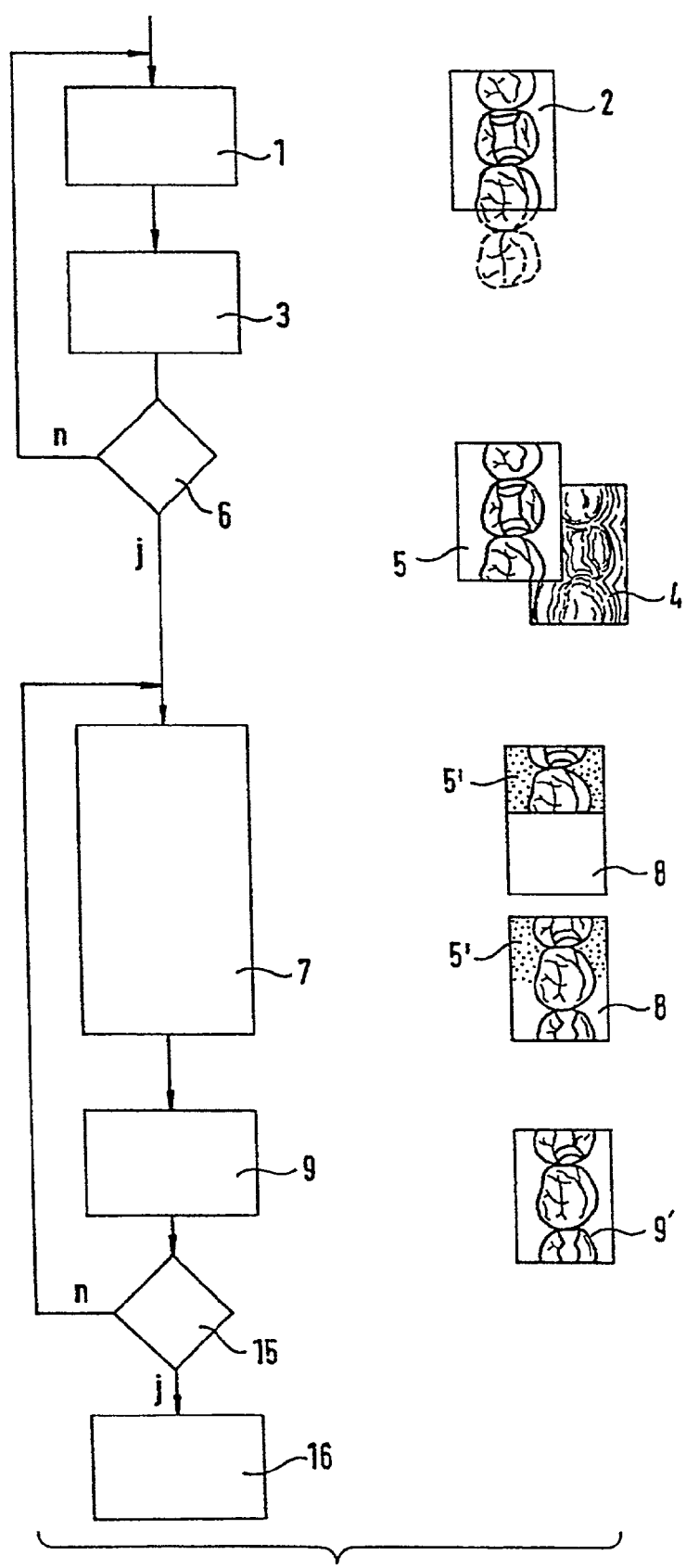
FIG. 1 is a flow diagram of the method sequence for measuring a dental arch of a first and of a second recording.

The first recording, already described in EP 0 250 993 B1, is initiated by a search phase preceding the actual measurement operation. This process is shown in accordance with the flow diagram from FIG. 1. In this search phase 1, a measurement camera initially operates like a conventional video system. The tooth part which appears in the recording window is registered by an imaging optical system and sensor, and is represented on a monitor as a standard television image 2. The observed tooth is illuminated by the camera for the purpose of spatial measurement, to be precise with a grid-like reference pattern. However, this reference pattern should not also appear on the search image, since the actual image content is thereby superposed. Therefore, the pattern is eliminated. The camera is oriented using the video search image in such a way that the measurements required for the measurement operation can be carried out successfully. If the production of a fitting for a tooth reconstruction is involved, then the positioning of the camera in the search phase 1 is to be chosen in such a way that it corresponds to the later entry axis of the fitting.

In the next step 3, the recording is initiated after the suitable position has been found. During the measurement operation, the reference pattern is projected onto the tooth surface in different spatial positions. The resulting images are stored in a memory. Altogether, this takes less than ⅕ of a second. Afterward, the stored information is transformed and stored as relief 4 in the form of depth data for each pixel. In addition, a contrast image 5 is generated which can be directly represented on the monitor. In its pseudo-plastic nature, this image 1 is like the video search image and thereby allows the dentist to effect immediate monitoring 6 of the recording.

According to the invention, a second recording 7 is then prepared. After the generation of the first recording, the contrast image 5 is inserted as a still image on the monitor in the region of the current video search image. During the orientation of the camera, at least a part 5' of the first contrast image and also the actual video search image 8 are displayed on the monitor in the same window. Using the structures represented in the first contrast image 5', it is possible to orient the current video search image 8 in such a way that sub-areas of the image are brought into congruence.

In this position, the second recording 9 is initiated and the recording is represented in the same window 9' of the monitor without the first contrast image.

If the monitoring 15 of the recording is satisfactory, then, in a further step 16, a computational, automatic correlation of the depth values for the overlapping areas is performed. This step uses the data of the first and second recordings that are related to one another. The superposed correlated relief is stored in the memory.

FIG. 1 illustrates a method sequence in which the second recording is carried out, relative to the first recording, with an object displaced by about half of the first image. This is explained in more detail with regard to FIGS. 2 to 4.

Teeth, 10, 11, 12, of a row of teeth are represented as objects to be measured in FIG. 2. The tooth 10 and approximately half of the tooth 11 being represented by means of a camera as video search image within a window 13 on a monitor (not illustrated). The area represented in the window 13 is measured by means of the camera in a first recording after the latter has been oriented using the video search image in accordance with the requirements for the measurement operation. From the data record generated by the camera, a contrast image is produced and depth data are generated. In terms of its information content, the contrast image corresponds approximately to the video search image, so that the operator can check the quality of the recording. This contrast image is represented in the window 13 after the recording.

In order to measure the tooth 11, the second recording is then prepared by the contrast image of FIG. 2 being displaced within the window 13 by approximately half of the image length away from the object 11 to be measured. Thus an area 21 is produced in which there is initially no image information present, represented in FIG. 3.

In part of the contrast image fo the first recording, the camera is aligned with the tooth 11 that is to be measured. Also, the video search image of the second recording to be prepared is displayed in the upper area 22 of the window 13. By contrast, the current moving video search image is represented in the area 21 of the window 13. By displaying the first contrast image in the area 22, it is possible to orient the current video search image in such a way that parts of the tooth 10 and 11 which are represented in the contrast image and in the search image overlap and are brought into congruence such that it is possible to attach the second recording created afterward.

Figure 5:
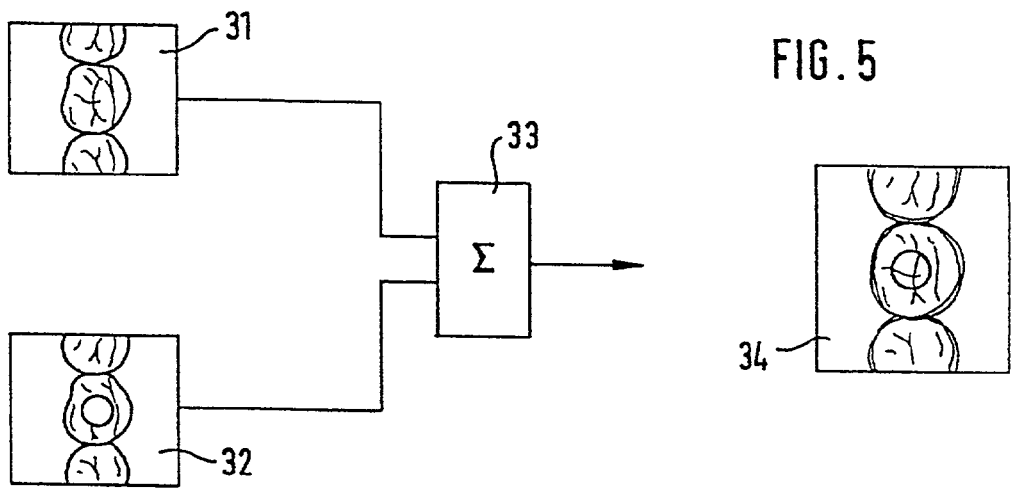
FIG. 5 is a diagram showing additive mixing of the still image with the search image.
Figure 6:
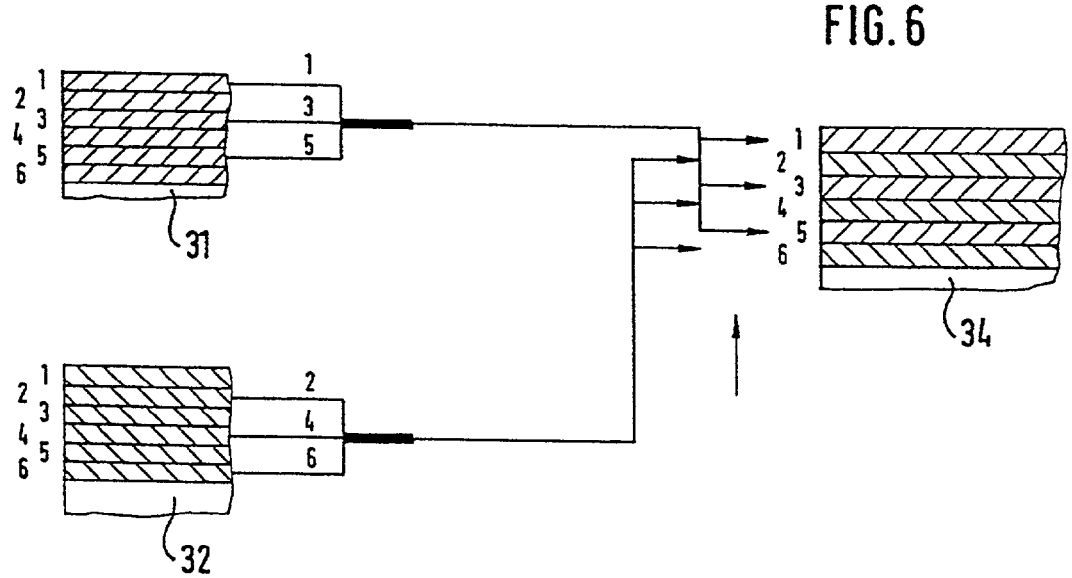
FIG. 6 is a diagram showing the row-by-row intermeshing of the still image with the search image.
Figure 7:
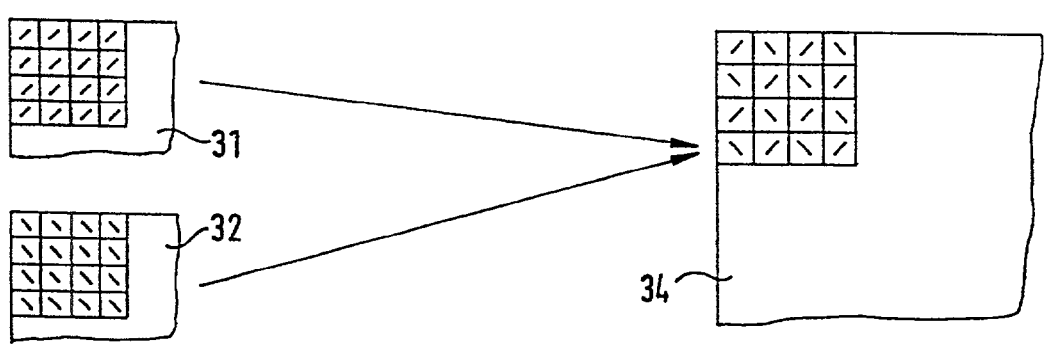
FIG. 7 is a diagram showing the intermeshing of the still image with the search image point by point like in a chessboard.

In order to be able to bring the moving video search image into congruence with the first contrast image, a semi-transparent representation of the first image is preferred. The semi-transparent representation can be realized in different ways, e.g., the image information items of both recordings can be additively mixed. Such mixing is represented in FIG. 5. Proceeding from the still image 31, stored in a memory, and the search image 32 currently recorded by the camera, the image information items are added point by point by means of a summer 33, and displayed as image 34. A further possibility consists in the representation 34 of the image information items alternating row by row or column by column, so that rows 1, 3, 5, 7, represent the image information items of the still image 31, and rows 2, 4, 6, 8, represent the image information items of the search image 32. Such a representation 34 is referred to as intermeshing and takes place only where both images yield information, that is to say in the area 22 of the window 13 (FIG. 3). In the area 21, where only one image, namely the current video search image, yields information, the latter is exclusively represented. Instead of row-by-row intermeshing, point-by-point intermeshing can also be effected, by a procedure in which individual points of the images 31, 32 are contained alternately in the representation 34, thereby producing a type of chessboard pattern (FIG. 7).

By virtue of the possibility of stringing together a plurality of recordings and the transmission of the depth data measured, it is possible to measure significantly larger areas beyond the image zone to be measured by the camera and to use them as a model of the entire object which is co-ordinated among the individual recordings.

What is claimed is:

1. A method for detecting and representing one or more objects using a camera, said method comprising the steps of:
   creating a first recording;
   producing a still image;
   inserting the still image into a current, moving search image in at least one sub-area, so that both images are recognizable;
   positioning the camera in such a way that the search image attains congruence with the inserted still image in said at least one sub-area; and
   initiating a second recording,
   wherein the recordings yield a three-dimensional data record containing depth values, the first and second recordings are correlated with one another computationally using the depth values of a common area, the still image is displaced and rotated by at least one of a predetermined distance and a predetermined angle, and is superposed on the moving search image only in said at least one sub-area, and the first and second recordings are displaced and rotated by at least $\frac{1}{10}$ of the extent of the recording in one direction relative to one another.

2. The method as claimed in claim 1, wherein:
   the first and second recordings essentially relate to the same object, the recordings being made from different directions.

3. The method as claimed in claim 1, wherein:
   the object to be recorded in the second recording has been altered, the surroundings of the altered object essentially being unchanged.

4. The method as claimed in claim 1, wherein:
   the displacement and rotation are effected in a manner dependent on the area to be recessed using an anatomical knowledge about the expected image information of the second recording.

5. The method as claimed in claim 1, wherein:
   the first recording is inserted semi-transparently into the search image.

6. The method as claimed in claim 1, wherein:
   a semi-transparent superposition of the still image and moving search image is produced by additive mixing.

7. The method as claimed in claim 1, wherein:
   the still image and the moving search image are represented in such a way that the image information items alternate row by row, or column by column or point by point.

8. The method as claimed in claim 5, wherein:
   the superposition of the image information items takes place only in the areas where both images yield information items, and at the locations where only one image yields information, this image is exclusively represented.

9. The method as claimed in claim 5, wherein:
the still image is represented in one hue in the superposition, and the search image is represented in another hue.

10. The method as claimed in claim 5, further comprising the step of:
modifying the still image by image-processing means for improving recognition accuracy of the still image.

11. The method as claimed in claim 9, wherein:
the hue of the still image is red, and
the hue of the search image is black or white.

12. The method as claimed in claim 1, wherein:
the objects include at least one of teeth, their preparations and their immediate vicinity.

* * * * *